(12) United States Patent
Löffler et al.

(10) Patent No.: US 7,186,405 B2
(45) Date of Patent: *Mar. 6, 2007

(54) DEODORANTS AND ANTI-PERSPIRANTS

(75) Inventors: Matthias Löffler, Niedernhausen (DE); Roman Morschhäuser, Mainz (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 540 days.

This patent is subject to a terminal disclaimer.

(21) Appl. No.: 10/433,113

(22) PCT Filed: Nov. 28, 2001

(86) PCT No.: PCT/EP01/13863

§ 371 (c)(1), (2), (4) Date: Nov. 17, 2003

(87) PCT Pub. No.: WO02/43687

PCT Pub. Date: Jun. 6, 2002

(65) Prior Publication Data

US 2004/0096409 A1    May 20, 2004

(30) Foreign Application Priority Data

Dec. 1, 2000 (DE) ............................. 100 59 823

(51) Int. Cl.
  *A61Q 15/00* (2006.01)
  *A61K 8/02* (2006.01)
  *A61K 31/74* (2006.01)

(52) U.S. Cl. .................. 424/65; 424/78.02; 424/78.08; 424/400; 424/401

(58) Field of Classification Search .................. 424/65, 424/78.02, 78.08, 400, 401
See application file for complete search history.

(56) References Cited

U.S. PATENT DOCUMENTS

| 5,368,850 A | 11/1994 | Cauwet et al. ................ 424/70 |
| 5,879,718 A * | 3/1999 | Sebillote-Arnaud ........ 424/70.5 |
| 6,001,379 A | 12/1999 | Grait .......................... 424/401 |
| 6,120,780 A | 9/2000 | Dupuis et al. .............. 424/401 |
| 6,524,564 B1 * | 2/2003 | Kim et al. ................ 424/70.12 |
| 6,833,419 B2 * | 12/2004 | Morschhauser et al. .... 526/288 |
| 7,025,973 B2 * | 4/2006 | Loffler et al. ............... 424/400 |

FOREIGN PATENT DOCUMENTS

| EP | 0 510 246 | 10/1992 |
| EP | 0 522 756 | 1/1993 |
| EP | 0 603 019 | 6/1994 |
| EP | 0 642 781 | 3/1995 |
| EP | 0 815 828 | 1/1998 |
| WO | WO 98/58625 | 12/1998 |
| WO | WO 00/12588 | 3/2000 |
| WO | WO 01/62214 | 8/2001 |

OTHER PUBLICATIONS

English abstract for JP 2001-278982, Oct. 10, 2001.
English Translation of PCT IPER for PCT/EP01/13863, Dated Mar. 11, 2003.

* cited by examiner

*Primary Examiner*—Shelley A. Dodson
(74) *Attorney, Agent, or Firm*—Richard P. Silverman

(57) ABSTRACT

The invention relates to deodorants and antiperspirants comprising at least one copolymer. The copolymer is obtained by free-radical copolymerization of A) acryloyldimethyltaurine and/or acryloyldimethyltaurates, and
B) optionally, one or more further olefinically unsaturated, noncationic comonomers,
C) optionally, one or more olefinically unsaturated, cationic comonomers,
D) optionally, one or more silicon-containing component(s),
E) optionally, one or more fluorine-containing component(s),
F) optionally, one or more macromonomers,
G) optionally, the copolymerization taking place in the presence of at least one polymeric additive,
H) with the proviso that component A) is copolymerized with at least one component selected from one of the groups D) to G).

27 Claims, No Drawings

DEODORANTS AND ANTI-PERSPIRANTS

The present invention relates to deodorants and antiperspirants comprising comb copolymers based on acryloyldimethyltaurine.

Deodorants and antiperspirants are offered in various forms, such as gels, sticks, creams, sprays or powders. The purpose of cosmetic deodorants is to eliminate body odor, which develops when perspiration, which is odorless per se, is broken down by microorganisms. The customary cosmetic deodorants are based on different principles of action.

In those known as antiperspirants the development of perspiration can be reduced by means of astringents—examples being aluminum salts such as aluminum hydroxychloride. Through the use of antimicrobial substances in cosmetic deodorants it is possible to reduce the bacterial flora on the skin. Ideally, only the odor-causing microorganisms should be actively reduced in this case. The combination of astringents with antimicrobial substances is also commonplace. Active antiperspirant substances in particular are frequently incompatible with common ingredients of deodorizing cosmetic and pharmaceutical preparations. For instance, deodorant sticks are generally formed of soap-glycol gels, since lower glycols and glycerol are able to form clear, transparent gels in the presence of sodium stearate, and these gels are additionally able to take up alcohol and water. Owing to the alkalinity of the soaps, acidic active substances, such as aluminum hydroxychloride, cannot be incorporated into such vehicles.

On account of these disadvantages, soap-free deodorants and antiperspirants have also been developed, based for example on liquid oils (e.g., paraffin oils, castor oil, isopropyl palmitate) thickened with semisolid constituents (e.g. vaseline, lanolin), solid constituents (e.g. beeswax, ceresin, microcrystalline waxes and/or ozokerite) and/or high-melting waxes (e.g., carnauba wax, candelilla wax). A disadvantage is that water-soluble active substances are frequently not sufficiently fat-soluble and consequently cannot be incorporated sufficiently into cosmetic bases. On the other hand, a certain water content is entirely desirable, in order to improve the compatibility of the compositions with the human skin or in order to enhance the solubility of saltlike ingredients. Suitable liquid oils include silicone oils, which give the compositions a very pleasant feeling on the skin. Such oils, however, are very expensive, exhibit disadvantages in the context of stable incorporation of water-soluble active substances, and are difficult to formulate in compositions of relatively high water content.

Surprisingly it has now been found that a new class of comb polymers based on acryloyldimethyltaurine (AMPS)—and suitable in the capacity of a thickener, bodying agent, emulsifier, solubilizer, dispersant, lubricant, adhesive, conditioner and/or stabilizer—are outstandingly suitable for the formulation of deodorants and antiperspirants.

The invention accordingly provides deodorants and antiperspirants comprising at least one copolymer obtainable by free-radical copolymerization of A) acryloyldimethyltaurine and/or acryloyldimethyltaurates, B) if desired, one or more further olefinically unsaturated, noncationic, optionally crosslinking comonomers which have at least one oxygen, nitrogen, sulfur or phosphorus atom and possess a molecular weight of less than 500 g/mol, C) if desired, one or more olefinically unsaturated, cationic comonomers which have at least one oxygen, nitrogen, sulfur or phosphorus atom and possess a molecular weight of less than 500 g/mol, D) if desired, one or more silicon-containing components capable of free-radical polymerization and having a functionality of at least one, E) if desired, one or more fluorine-containing components capable of free-radical polymerization and having a functionality of at least one, F) if desired, one or more olefinically mono- or polyunsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E), G) the copolymerization taking place if desired in the presence of at least one polymeric additive having number-average molecular weights of from 200 g/mol to $10^9$ g/mol, H) with the proviso that component A) is copolymerized with at least one component selected from one of the groups D) to G).

The copolymers of the invention preferably possess a molecular weight of from $10^3$ g/mol to $10^9$ g/mol, more preferably from $10^4$ to $10^7$ g/mol, with particular preference from $5*10^4$ to $5*10^6$ g/mol.

The acryloyldimethyltaurates can be the organic or inorganic salts of acryloyldimethyltaurine (acrylamidopropyl-2-methyl-2-sulfonic acid). Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines are independently of one another $(C_1-C_{22})$-alkyl radicals or $(C_2-C_{10})$-hydroxyalkyl radicals. Preference is also given to mono- to triethoxylated ammonium compounds with different degrees of ethoxylation. It should be noted that mixtures of two or more of the abovementioned representatives are also embraced by the invention.

The degree of neutralization of the acryloyldimethyltaurine can be between 0 and 100%, with particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyldimethyltaurine and/or acryloyidimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 30.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkyl-ammonium, dialkylammonium, trialkylammonium and/or tetraalkylammonium radicals, in which the alkyl substituents of the amines independently of one another are $(C_1-C_{22})$-alkyl radicals or $(C_2-C_{10})$-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl]succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable comonomers C) include all olefinically unsaturated monomers with cationic charge which are capable of forming copolymers with acryloyldimethyltaurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine, zwitterionic or amphoteric structure.

Comonomers C) for the purposes of the invention are also amino-functionalized precursors which can be converted by polymer-analogous reactions into their corresponding quaternary derivatives (e.g., reaction with dimethyl sulfate, methyl chloride), zwitterionic derivatives (e.g., reaction with hydrogen peroxide), betaine derivatives (e.g., reaction with chloroacetic acid), or amphoteric derivatives.

Particularly preferred comonomers C) are
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide and/or
methacryloylethylbetaine.

The weight fraction of the comonomers C), based on the total mass of the copolymers, can be from 0.1 to 99.8% by weight, more preferably from 0.5 to 30% by weight, and very preferably from 1 to 20% by weight.

Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicone-containing components are those of formula (I).

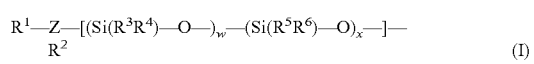

$$R^1-Z-[(Si(R^3R^4)-O-)_w-(Si(R^5R^6)-O)_x-]-R^2 \quad (I)$$

In this formula $R^1$ represents a polymerizable function from the group of the vinylically unsaturated compounds which is suitable for the synthesis of polymeric structures by a free-radical route. $R^1$ represents preferably a vinyl, allyl, methallyl, methylvinyl, acryloyl ($CH_2=CH-CO-$), methacryloyl ($CH_2=C[CH_3]-CO-$), crotonyl, senecionyl, itaconyl, maleyl, fumaryl or styryl radical.

The attachment of the silicone-containing polymer chain to the reactive end group $R^1$ requires a suitable chemical bridge Z. Preferred bridges Z are $-O-$, $-((C_1-C_{50})$-alkylene)-, $-((C_6-C_{30})$arylene)-, $-((C_5-C_8)$cycloalkylene)-, $-((C_1-C_{50})$alkenylene)-, -(polypropylene oxide)$_n$-, -(polyethylene oxide)$_o$-, -(polypropylene oxide)$_n$(polyethylene oxide)$_o$-, where n and o independently of one another denote numbers from 0 to 200 and the distribution of the EO/PO units can be random or in the form of blocks. Further suitable bridge groups Z are $-((C_1-C_{10})$alkyl)-(Si(OCH_3)_2)-$ and $-(Si(OCH_3)_2)-$.

The polymeric central moiety is represented by silicone-containing repeating units. The radicals $R^3$, $R^4$, $R^5$, and $R^6$ denote independently of one another $-CH_3$, $-O-CH_3$, $-C_6H_5$ or $-O-C_6H_5$.

The indices w and x represent stoichiometric coefficients which amount independently of one another to from 0 to 500, preferably 10 to 250.

The distribution of the repeating units across the chain can be not only purely random but also blocklike, alternating or gradientlike.

$R^2$ stands firstly for an aliphatic, olefinic, cycloaliphatic, arylaliphatic or aromatic ($C_1-C_{50}$) hydrocarbon radical (linear or branched) or $-OH$, $-NH_2$, $-N(CH_3)_2$, $-R^7$ or for the structural unit $[-Z-R^1]$. The definition of the two variables Z and $R^1$ has already been explained. $R^7$ stands for further Si-containing groups. Preferred radicals $R^7$ are $-O-Si(CH_3)_3$, $-O-Si(Ph)_3$, $-O-Si(O-Si(CH_3)_3)_2CH_3$) and $-O-Si(O-Si(Ph)_3)_2Ph)$.

If $R^2$ is an element of the group $[-Z-R^1]$ the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following components with acrylic or methacrylic modification:

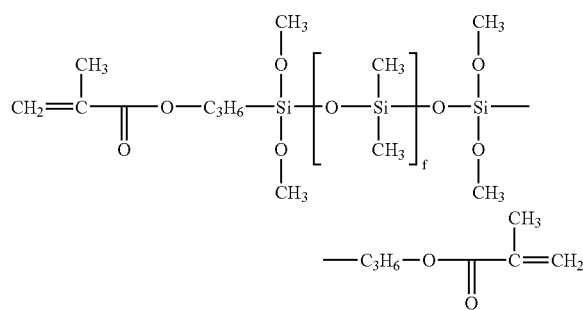

methacryloyloxypropyldimethylsilyl-endblocked polydimethylsiloxanes (f=2 to 500)

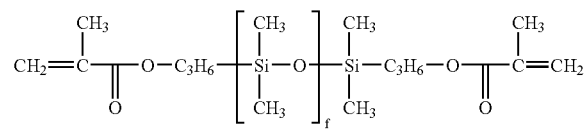

methacryloyloxypropyl-endblocked polydimethylsiloxanes (f=2 to 500)

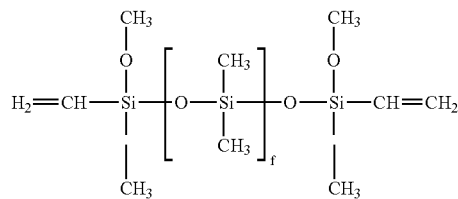

vinyidimethoxysilyl-endblocked polydimethylsiloxanes (f=2–500)

Based on the total mass of the copolymers, the amount of silicon-containing components can be up to 99.8% by weight, preferably from 0.5 to 30% by weight, more preferably from 1 to 20% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked.

Preferred fluorine-containing components E) are those of formula (II).

$$R^1—Y—C_rH_{2r}C_sF_{2s}CF_3 \qquad (II)$$

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical.

The attachment of the fluorine-containing group to the reactive end group $R^1$ requires a suitable chemical bridge Y. Preferred bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$–$C_{50}$)alkyl-O—, —O-phenyl-O—, —O-benzyl-O—, —O—($C_5$–$C_8$)cycloalkyl-O—, —O—($C_1$–$C_{50}$)alkenyl-O—, —O—(CH($CH_3$)—$CH_2$—O—)$_n$—, —O—($CH_2$—$CH_2$—O)$_n$—, and —O—([CH—$CH_2$—O]$_n$—[$CH_2$—$CH_2$—O]$_m$)$_o$—, where n, m, and o independently of one another denote numbers from 0 to 200 and the distribution of the EO and PO units can be random or in the form of blocks. r and s are stoichiometric coefficients which independently of one another denote numbers from 0 to 200.

Preferred fluorine-containing components E) of formula (II) are
perfluorohexylethanol methacrylate,
perfluorohexoylpropanol methacrylate,
perfluoroctylethanol methacrylate,
perfluoroctylpropanol methacrylate,
perfluorohexylethanolyl polyglycol ether methacrylate,
perfluorohexoylpropanolyl poly[ethylglycol-co-propylene glycol ether] acrylate,
perfluoroctylethanolyl poly[ethylglycol-block-co-propylene glycol ether] methacrylate,
perfluoroctylpropanolyl polypropylene glycol ether methacrylate.

Based on the total mass of the copolymers the amount of fluorine-containing components can be up to 99.9% by weight, preferably from 0.5 to 30% by weight, more preferably from 1 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers. Preferred macromonomers F) are compounds of formula (III).

$$R^1—Y—[(A)_v—(B)_w—(C)_x—(D)_z]—R^2 \qquad (III)$$

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

Attachment of the polymer chain to the reactive end group requires a suitable bridging group Y. Preferred bridges Y are —O—, —C(O)—, —C(O)—O—, —S—, —O—$CH_2$—CH(O—)—$CH_2$OH, —O—$CH_2$—CH(OH)—$CH_2$O—, —O—$SO_2$—O—, —O—$SO_2$—O—, O—SO—O—, —PH—, —P($CH_3$)—, —$PO_3$—, —NH—, and —N($CH_3$)—, more preferable —O—.

The polymeric central moiety of the macromonomer is represented by the discrete repeating units A, B, C, and D. Preferably the repeating units A, B, C, and D are derived from: acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D. v, w, x, and z amount independently of one another to from 0 to 500, preferably 1 to 30, it being necessary for the sum of the four coefficients on average to be $\geq 1$.

The distribution of the repeating units over the macromonomer chain can be random, blocklike, alternating or gradientlike.

$R^2$ denotes a linear or branched aliphatic, olefinic, cycloaliphatic, arylaliphatic or aromatic ($C_1$–$C_{50}$) hydrocarbon radical, OH, —$NH_2$, —$N(CH_3)_2$ or is the structural unit [—Y—$R^1$].

In the case of $R^2$ being [—Y—$R^1$] the macromonomers in question are difunctional and suitable for crosslinking the copolymers.

Particularly preferred macromonomers F) are acrylically or methacrylically monofunctionalized alkyl ethoxylates of formula (IV).

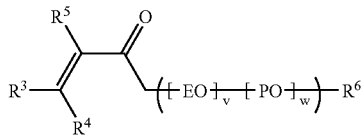

(IV)

$R_3$, $R_4$, $R_5$, and $R_6$ are independently of one another hydrogen or n-aliphatic, iso-aliphatic, olefinic, cycloaliphatic, arylaliphatic or aromatic ($C_1$–$C_{30}$) hydrocarbon radicals.

Preferably $R_3$ and $R_4$ are H or —$CH_3$, more preferably H; $R_5$ is H or —$CH_3$; and $R_6$ is an n-aliphatic, iso-aliphatic, olefinic, cycloaliphatic, arylaliphatic or aromatic ($C_1$–$C_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the abovementioned bridges.

Further particularly preferred macromonomers F) have the following structure in accordance with formula (IV):

| Name | $R^3$ | $R^4$ | $R^5$ | $R^6$ | v | w |
|---|---|---|---|---|---|---|
| ® LA-030 methacrylate | H | H | —$CH_3$ | -lauryl | 3 | 0 |
| ® LA-070 methacrylate | H | H | —$CH_3$ | -lauryl | 7 | 0 |
| ® LA-200 methacrylate | H | H | —$CH_3$ | -lauryl | 20 | 0 |
| ® LA-250 methacrylate | H | H | —$CH_3$ | -lauryl | 25 | 0 |
| ® T-080 methacrylate | H | H | —$CH_3$ | -talc | 8 | 0 |
| ® T-080 acrylate | H | H | H | -talc | 8 | 0 |
| ® T-250 methacrylate | H | H | —$CH_3$ | -talc | 25 | 0 |
| ® T-250 crotonate | —$CH_3$ | H | —$CH_3$ | -talc | 25 | 0 |
| ® OC-030 methacrylate | H | H | —$CH_3$ | -octyl | 3 | 0 |
| ® OC-105 methacrylate | H | H | —$CH_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | —$CH_3$ | —$CH_3$ | H | -behenyl | 10 | 0 |
| ® PEG-440 diacrylate | H | H | H | -acryloyl | 10 | 0 |
| ® B-11-50 methacrylate | H | H | —$CH_3$ | -butyl | 17 | 13 |
| ® MPEG-750 methacrylate | H | H | —$CH_3$ | -methyl | 18 | 0 |
| ® P-010 acrylate | H | H | H | -phenyl | 10 | 0 |
| ® O-050 acrylate | H | H | H | -oleyl | 5 | 0 |

Further particularly suitable macromonomers F) are esters of (meth)acrylic acid with
($C_{10}$–$C_{18}$) fatty alcohol polyglycol ethers having 8 EO units (Genapol® C-080)
$C_{11}$ oxo alcohol polyglycol ethers having 8 EO units (Genapol® UD-080)
($C_{12}$–$C_{14}$) fatty alcohol polyglycol ethers having 7 EO units (Genapol® LA-070)
($C_{12}$–$C_{14}$) fatty alcohol polyglycol ethers having 11 EO units (Genapol® LA-110)
($C_{16}$–$C_{18}$) fatty alcohol polyglycol ethers having 8 EO units (Genapol® T-080)
($C_{16}$–$C_{18}$) fatty alcohol polyglycol ethers having 15 EO units (Genapol® T-150)
($C_{16}$–$C_{18}$) fatty alcohol polyglycol ethers having 11 EO units (Genapol® T-110)
($C_{16}$–$C_{18}$) fatty alcohol polyglycol ethers having 20 EO units (Genapol® T-200)
($C_{16}$–$C_{18}$) fatty alcohol polyglycol ethers having 25 EO units (Genapol® T-250)
($C_{18}$–$C_{22}$) fatty alcohol polyglycol ethers having 25 EO units and/or
iso-($C_{16}$–$C_{18}$) fatty alcohol polyglycol ethers having 25 EO units.

The Genapol® grades are products of Clariant GmbH.

The molecular weight of the macromonomers F) is preferably from 200 g/mol to $10^6$ g/mol, more preferably from 150 to $10^4$ g/mol, and very preferably from 200 to 5000 g/mol.

Based on the total mass of the copolymers it is possible to use suitable macromonomers at up to 99.8% by weight. The ranges used are preferably from 0.5 to 30% by weight and from 70 to 99.5% by weight. Particularly preferred are fractions of from 1 to 20% by weight and from 75 to 95% by weight.

Preferred copolymers are those obtainable by copolymerizing at least components A), C) and D).

Further preferred copolymers are those obtainable by copolymerizing at least components A), C) and E).

Further preferred copolymers are those obtainable by copolymerizing at least components A), D) and F).

Further preferred copolymers are those obtainable by copolymerizing at least components A) and F).

Further preferred copolymers are those obtainable by copolymerizing at least components A) and D).

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention. Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols, preferably in t-butanol. The term "copolymers" also comprehends those having more than two different monomer types.

Particularly preferred additives G) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyidimethylammonium chloride (DADMAC) and/or [2-(methacryloyloxy)ethyl]-trimethylammonium chloride (MAPTAC); polyalkylene glycols and/or alkylpolyglycols.

Particularly preferred additives G) are polyvinylpyrrolidones (e.g., Luviskol K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

In another preferred embodiment the copolymers of the invention are crosslinked, i.e., they contain comonomers having at least two polymerizable vinyl groups. Preferred crosslinkers are methylenebisacrylamide; methylenebismethacrylamide; esters of unsaturated monocarboxylic and polycarboxylic acids with polyols, preferably diacrylates and triacrylates, dimethacrylates and trimethacrylates, more preferably butanediol and ethylene glycol diacrylate and methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. A particularly preferred crosslinker is trimethylolpropane triacrylate (TMPTA).

The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electromagnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example.

Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

Serving as the polymerization medium may be any solvents which are very substantially inert in respect of free-radical polymerization reactions and which allow the development of high molecular weights. Use is preferably made of water and lower, tertiary alcohols or hydrocarbons having 3 to 30 carbon atoms. In one particularly preferred embodiment t-butanol is used as the reaction medium. Mixtures of two or more representatives of the potential solvents described are of course likewise in accordance with the invention. This also includes emulsions of mutually immiscible solvents (e.g., water/hydrocarbons). In principle, all kinds of reaction regime leading to the polymer structures of the invention are suitable (solution polymerization, emulsion methods, precipitation methods, high-pressure methods, suspension methods, bulk polymerization, gel polymerization, and so on).

Preferred suitability is possessed by precipitation polymerization, particularly preferred suitability by precipitation polymerization in tert-butanol.

The following list shows 67 copolymers with particular suitability for formulating the compositions of the invention. The different copolymers 1 to 67 are obtainable in accordance with the following preparation processes 1, 2, 3, and 4.

Process 1

These polymers can be prepared by the precipitation method in tert-butanol. The monomers were introduced in t-butanol, the reaction mixture was rendered inert, and then, after initial heating to 60° C., the reaction was initiated by addition of the corresponding t-butanol-soluble initiator (preferably dilauroyl peroxide). After the end of reaction (2 hours) the polymers were isolated by removal of the solvent under suction and by subsequent vacuum drying.

Process 2

These polymers are preparable by the gel polymerization method in water. The monomers are dissolved in water, the reaction mixture is rendered inert, and then, after initial heating to 65° C., the reaction is initiated by addition of suitable initiators or initiator systems (preferably $Na_2S_2O_8$). The polymer gels are subsequently comminuted and the polymers are isolated after drying.

Process 3

These polymers are preparable by the emulsion method in water. The monomers are emulsified in a mixture of water/organ solvent (preferably cyclohexane) using an emulsifier, the reaction mixture is rendered inert by means of $N_2$, and then, after initial heating to 80° C., the reaction is initiated by addition of suitable initiators or initiator systems (preferably $Na_2S_2O_8$). The polymer emulsions are subsequently evaporated down (with cyclohexane acting as an azeotrope former for water) and the polymers are thereby isolated.

Process 4

These polymers are preparable by the solution method in organic solvents (preferably toluene, also, for example, tertiary alcohols). The monomers are introduced in the solvent, the reaction mixture is rendered inert, and then, after initial heating to 70° C., the reaction is initiated by addition of suitable initiators or initiator systems (preferably dilauroyl peroxide). The polymers are isolated by evaporating off the solvent and by subsequent vacuum drying.

Polymers having hydrophobic side chains, uncrosslinked

| No. | Composition | Preparation process |
|---|---|---|
| 1 | 95 g AMPS 5 g Genapol T-080 | 1 |
| 2 | 90 g AMPS 10 g Genapol T-080 | 1 |
| 3 | 85 g AMPS 15 g Genapol T-080 | 1 |
| 4 | 80 g AMPS 20 g Genapol T-080 | 1 |
| 5 | 70 g AMPS 30 g Genapol T-080 | 1 |
| 6 | 50 g AMPS 50 g Genapol T-080 | 3 |
| 7 | 40 g AMPS 60 g Genapol T-080 | 3 |
| 8 | 30 g AMPS 70 g Genapol T-080 | 3 |
| 9 | 20 g AMPS 80 g Genapol T-080 | 3 |
| 10 | 60 g AMPS 60 g BB10 | 4 |
| 11 | 80 g AMPS 20 g BB10 | 4 |
| 12 | 90 g AMPS 10 g BB10 | 3 |
| 13 | 80 g AMPS 20 g BB10 | 1 |
| 14 | 80 g AMPS 20 g Genapol LA040 | 1 |

Polymers having hydrophobic side chains, crosslinked

| No. | Composition | Preparation process |
|---|---|---|
| 15 | 80 g AMPS 20 g Genapol LA040 0.6 g AMA | 1 |
| 16 | 80 g AMPS 20 g Genapol LA040 0.8 g AMA | 1 |
| 17 | 80 g AMPS 20 g Genapol LA040 1.0 g AMA | 1 |
| 18 | 628.73 g AMPS 120.45 g Genapol T-250 6.5 g TMPTA | 2 |
| 19 | 60 g AMPS 40 g BB10 1.9 g TMPTA | 4 |
| 20 | 80 g AMPS 20 g BB10 1.4 g TMPTA | 4 |
| 21 | 90 g AMPS 10 g BB10 1.9 g TMPTA | 4 |
| 22 | 80 g AMPS 20 g BB10 1.9 g TMPTA | 4 |
| 23 | 60 g AMPS 40 g BB10 1.4 g TMPTA | 4 |

Polymers having hydrophobic side chains, crosslinked, grafted

| No. | Composition | Preparation process |
|---|---|---|
| 24 | 95 g AMPS 5 g BB10, 1.9 g TMPTA, 1 g Poly-NVP | 1 |
| 25 | 90 g AMPS 10 g BB10, 1.9 g TMPTA, 1 g Poly-NVP | 1 |
| 26 | 85 g AMPS 15 g BB10, 1.9 g TMPTA, 1 g Poly-NVP | 1 |
| 27 | 90 g AMPS 10 g BB10, 1.9 g TMPTA, 1 g Poly-NVP | 1 |

Polymers having silicon-containing groups, uncrosslinked

| No. | Composition | Preparation process |
|---|---|---|
| 28 | 80 g AMPS, 20 g Silvet 867 | 1 |
| 29 | 80 g AMPS, 50 g Silvet 867 | 4 |

Polymers having silicon-containing groups, crosslinked

| No. | Composition | Preparation process |
|---|---|---|
| 30 | 80 g AMPS, 20 g Silvet 867, 0.5 g MBA | 4 |
| 31 | 80 g AMPS, 20 g Silvet 867, 1.0 g MBA | 1 |
| 32 | 60 g AMPS, 40 g Y-12867, 0.95 g AMA | 1 |
| 33 | 80 g AMPS, 20 g Y-12867, 0.95 g AMA | 1 |
| 34 | 90 g AMPS, 10 g Y-12867, 0.95 g AMA | 1 |
| 35 | 60 g AMPS, 40 g Silvet 7280, 0.95 g AMA | 1 |
| 36 | 80 g AMPS, 20 g Silvet 7280, 0.95 g AMA | 1 |
| 37 | 90 g AMPS, 10 g Silvet 7280, 0.95 g AMA | 1 |
| 38 | 60 g AMPS, 40 g Silvet 7608, 0.95 g AMA | 1 |
| 39 | 80 g AMPS, 20 g Silvet 7608, 0.95 g AMA | 1 |
| 40 | 90 g AMPS, 10 g Silvet 7608, 0.95 g AMA | 1 |

Polymers having hydrophobic side chains and cationic groups, uncrosslinked

| No. | Composition | Preparation process |
|---|---|---|
| 41 | 87.5 g AMPS, 7.5 g Genapol T-110, 5 g DADMAC | 2 |
| 42 | 40 g AMPS, 10 g Genapol T110, 45 g methacrylamide | 2 |
| 43 | 55 g AMPS, 40 g Genapol LA040, 5 g Quat | 1 |
| 44 | 75 g AMPS, 10 g BB10, 6.7 g Quat | 1 |

Polymers having hydrophobic side chains and cationic groups, crosslinked

| No. | Composition | Preparation process |
|---|---|---|
| 45 | 60 g AMPS, 20 g Genapol T-80, 10 g Quat, 10 g HEMA | 1 |
| 46 | 75 g AMPS, 20 g Genapol T-250, 5 g Quat, 1.4 g TMPTA | 1 |
| 47 | 75 g AMPS, 20 g Genapol T-250, 10 g Quat, 1.4 g TMPTA | 1 |
| 48 | 75 g AMPS, 20 g Genapol T-250, 20 g Quat, 1.4 g TMPTA | 1 |

Polymers having fluorine-containing groups

| No. | Composition | Preparation process |
|---|---|---|
| 49 | 94 g AMPS, 2.02 g Fluowet AC 600 | 1 |
| 50 | 80 g AMPS, 20 g perfluorooctylpolyethylene glycol methacrylate, 1 g Span 80 | 3 |

Polymers having fluorine-containing groups, grafted

| No. | Composition | Preparation process |
|---|---|---|
| 51 | 80 g AMPS, 10 g Fluowet AC 600, 5 g Poly-NVP | 1 |
| 52 | 70 g AMPS, 8 g perfluorooctylethyloxyglyceryl methacrylate, 5 g Poly-NVP | 4 |

Polyfunctional polymers

| No. | Composition | Preparation process |
|---|---|---|
| 53 | 80 g AMPS, 10 g Genapol LA070, 10g Silvet 7608, 1.8 g TMPTA | 1 |
| 54 | 70 g AMPS, 5 g N-vinylpyrrolidone, 15 g Genapol T-250 methacrylate, 10 g Quat, 10 g Poly-NVP | 4 |
| 55 | 80 g AMPS, 5 g N-vinylformamide, 5 g Genapol O-150 methacrylate, 10 g DADMAC, 1.8 g TMPTA, 8 g poly-N-vinylformamide | 2 |
| 56 | 70 g AMPS, 5 g N-vinylpyrrolidone, 15 g Genapol T-250 methacrylate, 10 g Quat, 10 g Poly-NVP | 1 |
| 57 | 60 g AMPS, 10 g Genapol-BE-020 methacrylate, 10 g Genapol T-250 acrylate, 20 g Quat, 1 g Span 80 | 1 |
| 58 | 60 g AMPS, 20 g MPEG-750 methacrylate, 10 g methacryloyloxypropyldimethicone, 10 g perfluorooctylpolyethylene glycol methacrylate, 10 g poly[N-vinylcaprolactone-co-acrylic acid] (10/90) | 1 |
| 59 | 80 g AMPS, 5 g N-vinylformamide, 5 g Genapol O-150 methacrylate, 10 g DADMAC, 1.8 g TMPTA | 1 |
| 60 | 70 g AMPS, 10 g Genapol T-250 acrylate, 5 g N-methyl-4-vinylpyridinium chloride, 2.5 g Silvet Y-12867, 2.5 g perfluorohexylpolyethylene glycol methacrylate, 10 g polyethylene glycol dimethacrylate, 4 g poly[N-vinylcaprolactam] | 1 |
| 61 | 10 g AMPS, 20 g acrylamide, 30 g N-2-vinylpyrrolidone, 20 g Silvet 7608, 10 g methacryloyloxypropyldimethicone, 10 g Fluowet AC 812 | 3 |
| 62 | 60 g AMPS, 10 g DADMAC, 10 g Quat, 10 g Genapol-LA-250 crotonate, 10 g methacryloyloxypropyldimethicone, 7 g poly[acrylic acid-co-N-vinylformamide] | 1 |
| 63 | 50 g AMPS, 45 g Silvet 7608, 1.8 g TMPTA, 8 g poly[N-vinylformamide] | 1 |
| 64 | 20 g AMPS, 10 g Genapol T 110, 35 g MAA, 30 g HEMA, 5 g DADMAC | 4 |
| 65 | 20 g AMPS, 80 g BB10, 1.4 g TMPTA | 1 |
| 66 | 75 g AMPS, 20 g BB10, 6.7 g Quat, 1.4 g TMPTA | 1 |
| 67 | 35 g AMPS, 60 g acrylamide, 2 g VIFA, 2.5 g vinylphosphonic acid, 2 mol % Fluowet EA-600 | 4 |

Chemical designation of the reactants:

| | |
|---|---|
| AMPS | acryloyldimethyltaurate, either Na or NH4 salt |
| Genapol ® T-080 | $C_{16}$–$C_{18}$ fatty alcohol polyglycol ether having 8 EO units |
| Genapol ® T-110 | $C_{12}$–$C_{14}$ fatty alcohol polyglycol ether having 11 EO units |
| Genapol ® T-250 | $C_{16}$–$C_{18}$ fatty alcohol polyglycol ether having 25 EO units |
| Genapol ® LA-040 | $C_{12}$–$C_{14}$ fatty alcohol polyglycol ether having 4 EO units |
| Genapol ® LA-070 | $C_{12}$–$C_{14}$ fatty alcohol polyglycol ether having 7 EO units |
| Genapol ® O-150 methacrylate | $C_{16}$–$C_{18}$ fatty alcohol polyglycol ether methacrylate having 15 EO units |
| Genapol ® LA-250 crotonate | $C_{12}$–$C_{14}$ fatty alcohol polyglycol ether crotonate having 25 EO units |
| Genapol ® T-250 methacrylate | $C_{16}$–$C_{18}$ fatty alcohol polyglycol ether methacrylate having 25 EO units |
| Genapol ® T-250 acrylate | $C_{16}$–$C_{18}$ fatty alcohol polyglycol ether acrylate having 25 EO units |
| BB10 ® | polyoxyethylene(10)behenyl ether |

-continued

| | |
|---|---|
| TMPTA | trimethylolpropanetriacrylate |
| Poly-NVP | poly-N-vinylpyrrolidone |
| Silvet ® 867 | siloxane-polyalkylene oxide copolymer |
| MBA | methylenebisacrylamide |
| AMA | allyl methacrylate |
| ®Y-12867 | siloxane-polyalkylene oxide copolymer |
| Silvet ® 7608 | polyalkylene oxide-modified heptamethyltrisiloxane |
| Silvet ® 7280 | polyalkylene oxide-modified heptamethyltrisiloxane |
| DADMAC | diallyldimethylammonium chloride |
| HEMA | 2-hydroxyethyl methacrylate |
| Quat | 2-(methacryloyloxy)ethyltrimethylammonium chloride |
| Fluowet ® AC 600 | perfluoroalkylethyl acrylate |
| Span ® 80 | sorbitan ester |

In one preferred embodiment the copolymers are water-soluble or water-swellable.

The described grafting of the copolymers with other polymers, which can be carried out optionally, leads to products having a particular polymer morphology and giving rise to optically clear gels in aqueous systems. A potential disadvantage of the copolymers without grafting is a more or less strong opalescence in aqueous solution. The basis for this opalescence is hitherto unavoidable, overcrosslinked polymer fractions which arise in the course of the synthesis and are inadequately swollen in water. This produces light-scattering particles whose size is well above the wavelength of visible light and which are therefore the cause of the opalescence. The described grafting process, which can be carried out optionally, substantially reduces or entirely prevents the formation of overcrosslinked polymer fractions in relation to conventional techniques.

The described incorporation both of cationic charges and of silicon, fluorine or phosphorus atoms into the copolymers, which can be carried out optionally, leads to products which in cosmetic formulations possess particular sensorial and rheological properties. An improvement in the sensorial and rheological properties may be advantageous in particular in the context of use in rinse-off products.

Silicon-modified copolymers can take over some or all of the functions of silicone oils. The use of silicones can be reduced or avoided by means of the copolymers.

The deodorants and antiperspirants of the invention, based on the finished compositions, contain preferably from 0.01 to 10% by weight, preferably from 0.1 to 5% by weight, very preferably from 0.5 to 3% by weight, of the copolymers.

The compositions of the invention preferably contain from 0.01 to 89% by weight, more preferably from 5 to 50% by weight, very preferably from 10 to 30% by weight, of water.

The compositions of the invention preferably contain up to 10% by weight, more preferably from 1 to 6% by weight, of glycerol.

The compositions of the invention preferably comprise active antimicrobial substances which inhibit the perspiration-decomposing microorganisms and/or the perspiration-decomposing esterase enzyme.

Of preferred suitability as active antimicrobial substances are cetyltrimethylammonium chloride, cetylpyridinium chloride, benzethonium chloride, diisobutylethoxyethyldimethylbenzylammonium chloride, sodium N-laurylsarcosinate, sodium-N-palmethylsarcosinate, lauroylsarcosine, N-myristoylglycine, potassium N-laurylsarcosine, trimethylammonium chloride, sodium aluminum chlorohydroxylactate, triethyl citrate, tricetylmethylammonium chloride, 2,4,4'-tri-chloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, for example, L-lysine hexadecyl amide, citrate heavy metal salts, salicylates, piroctoses, especially zinc salts, pyrithiones and their heavy metal salts, especially zinc pyrithione, zinc phenol sulfa, farnesol, and combinations of these active substances.

The compositions of the invention comprise the antimicrobial agents preferably in amounts of up to 50% by weight, more preferably from 0.01 to 10% by weight, very preferably from 0.1 to 10% by weight.

The compositions of the invention preferably comprise astringents. Preferred astringents are oxides, preferably magnesium oxide, aluminum oxide, titanium dioxide, zirconium dioxide, and zinc oxide, oxide hydrates, preferably aluminum oxide hydrate (boehmite) and hydroxides, preferably of calcium, magnesium, aluminum, titanium, zirconium or zinc.

The compositions of the invention comprise the active astringent substances in amounts of preferably from 0 to 50% by weight, more preferably from 0.01 to 10% by weight, and very preferably from 0.1 to 10% by weight.

The compositions of the invention further preferably comprise gelling agents. Suitable gelling agents include all surface-active substances which, when dissolved in the liquid phase, form a network structure and so solidify the liquid phase.

Suitable gelling agents are described, for example, in WO 98/58625.

Preferred gelling agents are metal salts of fatty acids, preferably having 12 to 22 carbon atoms, examples being sodium stearate, sodium palmitate, sodium laurate, sodium arachidate, sodium behenate, potassium stearate, potassium palmitate, sodium myristate, aluminum monostearate, hydroxy-fatty acids, examples being 12-hydroxystearic acid, -lauryl, 16-hydroxyhexadecanoyl acid; fatty acid amides; fatty acid alkanol amides; dibenzalsorbitol, and alcohol-soluble polyamides and polyacrylamides or mixtures of such.

The compositions of the invention preferably contain from 0.01 to 20% by weight, more preferably from 0.1 to 10% by weight, very preferably from 1 to 8% by weight, and with especial preference from 3 to 7% by weight, of gelling agents.

In a further preferred embodiment the compositions of the invention comprise further alcohols.

Preferred alcohols are alkoxylated alcohols having preferably 1 to 80, more preferably 3 to 20, alkoxy groups and at least one free hydroxyl group. Particular preference is given to ethanol, propanol, isopropanol, n-butanol, isobutanol, t-butanol, glycerol, diethylene glycol, triethylene glycol, dipropylene glycol, tripropylene glycol, liquid polypropylene-polyethylene glycol copolymers, tetrapropylene glycol, tetraethylene glycol, dibutylene glycol, trimethylene glyecol, diethylene glycol monoethyl ether, PEG-8, 1,3-butanediol, 1,4-butanediol, glyceryl propoxylate, propylene glycol, hexylene glycol, 1,2-hexanediol, 1,3-butylene glycol, 1,2,6-trihydroxyhexane, and 1,2,3-trihydroxyhexane. Further preferred alcohols are polyethylene glycols having a relative molecular mass of below 2000. Particular preference is given to using polyethylene glycol having a relative molecular mass between 200 and 600 in amounts of up to 45% by weight and polyethylene glycol having a relative molecular mass between 400 and 600 in amounts of from 5 to 25% by weight.

The compositions of the invention contain preferably from 5 to 90% by weight, more preferably from 5 to 80% by weight, and very preferably from 20 to 60% by weight, of alcohol.

Fragrance or perfume oils which may be used are individual odorant compounds, e.g., the synthetic products of the ester, ether, aldehyde, ketone, alcohol, and hydrocarbon type. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate, and benzyl salicylate. The ethers include, for example, benzyl ethyl ether; the aldehydes include, for example, the linear alkanals having 8 to 18 carbon atoms, citral, citronellal, citronellyloxyacetaldehyde, cyclamenaldehyde, hydroxycitronellal, lilial, and bourgeonal; the ketones include, for example, the ionones, alpha-isomethyl ionone and methyl cedryl ketone; the alcohols include anethole, citronellol, eugenol, geraniol, linalool, phenylethyl alcohol, and terpineol; the hydrocarbons include primarily the terpenes and balsams. Preference is given to using mixtures of different odorants which together produce a pleasing fragrance note.

Perfume oils may also comprise natural odorant mixtures, as are obtainable from vegetable or animal sources, e.g., pine oil, citrus oil, jasmine oil, lily oil, rose oil or ylang ylang oil. Essential oils of low volatility, which are mostly used as aroma components, are also suitable as perfume oils, examples being sage oil, chamomile oil, oil of cloves, melissa oil, mint oil, cinnamon leaf oil, lime blossom oil, juniper berry oil, vetiver oil, olibanum oil, galbanum oil, and laudanum oil.

As further auxiliaries and additives the compositions of the invention may comprise oily substances, emulsifiers and coemulsifiers, superfatting agents, moisturizing agents, stabilizers, active biogenic substances (local anesthetics, antibiotics, antiphlogistics, antiallergics, corticosteroids, sebostatics), vitamins, panthenol, allantoin, plant extracts, e.g., aloe vera, and proteins, glycerol, preservatives, pearlizing agents, dyes and fragrances, solvents, hydrotropic agents, enzymes, carrier substances, e.g., phyllosilicates, pyrogenic silica, electrolyte salts such as KCl, NaCl, complexing agents, antioxidants, and UV light protection filters.

An oily substance is any fatty substance which is liquid at room temperature (25° C.).

The fatty phase may comprise one or more oils selected preferably from the following oils:
a) silicone oils, volatile or nonvolatile, linear, branched or cyclic, optionally with organic modification, phenylsilicones, silicone resins and silicone gums, which are solid or liquid at room temperature;
b) mineral oils such as paraffin oil or vaseline oil;
c) oils of animal origin such as perhydrosqualene or lanolin;
d) oils of plant origin, such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, and coconut oil;
e) synthetic oils, such as purcellin oil, isoparaffins, linear and/or branched fatty alcohols and fatty acid esters, preferably guerbet alcohols having 6 to 18, preferably 8 to 10, carbon atoms; esters of linear ($C_6$–$C_{13}$) fatty acids with linear ($C_6$–$C_{20}$) fatty alcohols; esters of branched ($C_6$–$C_{13}$) carboxylic acids with linear ($C_6$–$C_{20}$) fatty alcohols, esters of linear ($C_6$–$C_{18}$) fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on ($C_6$–$C_{10}$) fatty acids;
f) esters, such as dioctyl adipate, diisopropyl dimer dilinoleate, propylene glycols/dicaprylate or waxes such as beeswax, paraffin wax or microwaxes, alone or in combination with hydrophilic waxes, such as cetylstearyl alcohol, for example;
g) fluorinated and perfluorinated oils;
h) fluorinated silicone oils;
i) mixtures of the aforementioned substances.

Suitable nonionogenic coemulsifiers include adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; $C_{12}$–$C_{18}$ fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-hydroxystearate, for example. Likewise suitable are mixtures of compounds from one or more of these classes of substance.

Examples of suitable ionogenic coemulsifiers include anionic emulsifiers, such as mono-, di- or tri-phosphoric esters, but also cationic emulsifiers such as mono-, di-, and tri-alkyl quats and their polymeric derivatives.

As superfatting agents it is possible to use substances such as, for example, polyethoxylated lanolin derivatives, lecithin derivatives, polyol fatty acid esters, monoglycerides, and fatty acid alkanol amides, the latter serving simultaneously as foam stabilizers. Moisturizers available include for example isopropyl palmitate, glycerol and/or sorbitol.

As stabilizers it is possible to use metal salts of fatty acids, such as magnesium, aluminum and/or zinc stearate, for example. Active biogenic substances are to be understood as including, for example, plant extracts and vitamin complexes.

The compositions of the invention can be blended with conventional ceramides, pseudoceramides, fatty acid N-alkylpolyhydroxyalkyl amides, cholesterol, cholesterol fatty acid esters, fatty acids, triglycerides, cerebrosides, phospholipids, and similar substances as a care additive.

In order to adjust the rheological properties of aqueous or solvent-based emulsions or suspensions, the technical literature specifies a multiplicity of different systems. Those known include, for example, cellulose ethers and other cellulose derivatives (e.g., carboxymethylcellulose, hydroxyethylcellulose), gelatin, starch and starch derivatives, sodium alginates, fatty acid polyethylene glycol esters, agar agar, tragacanth or dextrins. A variety of materials are employed as synthetic polymers, such as polyvinyl alcohols, polyacrylamides, polyvinylamides, polysulfonic acids, polyacrylic acid, polyacrylates, polyvinylpyrrolidone, polyvinyl methyl ether, polyethylene oxides, copolymers of maleic anhydride and vinyl methyl ether, and also various mixtures and copolymers of the aforementioned compounds, including their various salts and esters. These polymers may alternatively be crosslinked or noncrosslinked.

Examples of suitable UV filters include 4-aminobenzoic acid; 3-(4'-trimethylammonium) benzylideneboran-2-one methylsulfate; 3,3,5-trimethylcyclohexyl salicylate; 2-hydroxy-4-methoxybenzophenone; 2-phenylbenzimidazole-5-sulfonic acid and its potassium, sodium, and triethanolamine salts; 3,3'-(1,4-phenylenedimethine) bis(7,7-dimethyl-2-oxobicyclo[2.2.1]heptane-1-methanesulfonic acid and its salts; 1-(4-tert-butylphenyl)-3-(4-methoxyphenyl)propane-1,3-dione, 3-(4'-sulfo)benzylidene-bornan-2-one and its salts; 2-ethylhexyl 2-cyano-3,3-diphenylacrylate; polymer of N-[2(and 4)-(2-oxoborn-3-ylidenemethyl)benzyl]acrylamide; 2-ethylhexyl 4-methoxycinnamate; ethoxylated ethyl 4-aminobenzoate; isoamyl 4-methoxycinnamate; 2,4,6-tris [p-(2-ethylhexyloxycarbonyl)anilino]-1,3,5-triazine; 2-(2H-benzotriazol-2-yl)4-methyl-6-(2-methyl-3-(1,3,3,3-tetramethyl-1-(trimethylsilyloxy) silyloxy) disiloxanyl)propyl) phenol; 4,4'-[(6-[4-((1,1-dimethylethyl)aminocarbonyl) -phenylamino]-1,3,5-triazin-2,4-yl)diimino]bis(benz acid 2-ethylhexyl ester); 3-(4'-methylbenzylidene) D,L-camphor; 3-benzylidene camphor; 2-ethylhexyl salicylate; 2-ethylhexyl 4-dimethylaminobenzoate; hydroxy-4-methoxybenzophenone phenone-5-sulfonic acid (sulisobenzone) and the sodium salt; and/or 4-isopropylbenzyl salicylate.

Antioxidants available include for example superoxide dismutase, tocopherol (vitamin E), and ascorbic acid (vitamin C).

Examples of suitable preservatives include phenoxyethanol, parabens, pentanediol or sorbic acid.

As dyes it is possible to use the substances which are suitable and approved for cosmetic purposes.

The deodorants and antiperspirants are preferably lotions, creams, sticks (including multiphase sticks), sprays, roll-on preparations, and powders.

The compositions of the invention have a pH of preferably from 2 to 12, more preferably from 3 to 8.

The examples which follow serve to illustrate the invention, though without restricting it (all percentages are by weight). The copolymers used in the examples are representative of the particularly preferred copolymers 1 to 67 already listed in the description. They were prepared by the therein-indicated processes 1, 2, 3 or 4 using the preferred initiators and solvents.

EXAMPLE 1

Antiperspirant Cream

| | | |
|---|---|---|
| A | Cithrol GMS A/S | 15.0% |
| | Glyceryl stearate/PEG-100 stearate | |
| | Crodacol C90 EP | 5.0% |
| | Cetyl alcohol | |
| | Copolymer No. 61 | 2.0% |
| B | Water | ad 100% |
| | Sorbitol (70%) | 3.0% |
| | Sorbitol | |
| | Reach 501 soln. | 44.5% |
| | Aluminum chlorohydrate | |
| C | Perfume oil | q.s. |
| | Dyes | q.s. |
| | Fragrances | q.s. |

Preparation:
I Heat A and B without Reach 501 to 70 to 75° C.
II Leave to cool with stirring.
III Add Reach 501 at 50 to 55° C.
IV Add perfume oil at 40 to 45° C.
V Homogenize at 30 to 35° C.

EXAMPLE 2

Clear Antiperspirant Gel

| | | |
|---|---|---|
| A | Abil EM97 | 2.3% |
| | Dimethicone copolyol/cyclopentasiloxane | |
| | Abil B8839 | 6.9% |
| | Cyclopentasiloxane/cyclohexasiloxane | |
| | Abil K4 | 6.9% |
| | Cyclotetrasiloxane/cyclopentasiloxane | |
| | Copolymer No. 28 | 1.5% |
| B | Aloxicoll L | 40.0% |
| | Aluminum chlorohydrate | |
| | Propylene glycol | 25.0% |
| | Distilled water | ad 100% |
| | Perfume oil | q.s. |

Preparation:
I Mix components A and B separately.
II Add phase B slowly with stirring at room temperature to phase A.
III Homogenize.

EXAMPLE 3

W/O Antiperspirant Cream

| | | |
|---|---|---|
| A | Abil EM90 | 2.0% |
| | Cetyldimethicone/copolyol | |
| | Abil B 8839 | 20.0% |
| | Cyclopentasiloxane/cyclohexasiloxane | |
| | Copolymer No. 65 | 2.0% |
| B | Aloxicoll L | 17.0 |
| | Aluminum chlorohydrate | |
| | Distilled water | ad 100% |
| | Perfume oil | q.s. |
| | Preservative | q.s. |

Preparation:
I Add phase B slowly with stirring at room temperature to phase A.
II Homogenize.

EXAMPLE 4

O/W Deodorant Lotion

| A | Teginacid H | 3.0% |
|---|---|---|
|   | Glyceryl stearate/Ceteth-20 | |
|   | Tegosoft, liq. | 3.0% |
|   | Cetearyl octanoate | |
|   | Tegosoft CT | 3.0% |
|   | Caprylic/capric triglyceride | |
|   | Copolymer No. 30 | 0.75% |
| B | Glycerol | 3.0% |
|   | Water | ad 100 |
| C | Citric acid | 0.15% |
|   | Preservative | q.s. |
|   | Perfume oil | q.s. |

Preparation:
I Heat phase A and B separately to about 80° C.
II Combine phase A and phase B.
III Homogenize.
IV Cool to 30° C. with gentle stirring.
V Add phase C at below 40° C.

EXAMPLE 5

Alcohol-free Deodorant Roll-on (Opaque)

| A | Tegodeo CW 90 | 2.0% |
|---|---|---|
|   | Zinc ricinoleate/tetrahydroxypropyl-ethylenediamine/Laureth-3/propylene glycol polyethylene glycol(3)lauryl ether | 1.0% |
|   | Triethanolamine | 1.0% |
| B | Copolymer No. 18 | 1.2% |
|   | Distilled water | ad 100 |
| C | Tagat R 40 | 3.0% |
|   | PEG-40 hydrogenated castor oil | |
|   | Perfume oil | q.s. |
|   | Preservative | q.s. |
| D | Citric acid (50% in water) | 0.2% |

Preparation:
I Heat phases A and B separately to 80° C.
II Stir phase B into phase A and homogenize.
III Cool with slow stirring.
IV Add phase C at 30° C.
V Adjust the pH by means of phase D.

EXAMPLE 6

Roll-on Deodorant

| A | Copolymer No. 27 | 1.0% |
|---|---|---|
|   | Distilled water | ad 100 |
| B | Hydagen DCMF | 0.1 |
|   | Chitosan | |
|   | Glycolic acid | 1.5% |
|   | Glycerol (86%) | 2.0% |

Preparation:
I Add copolymer No. 27 slowly to the water with vigorous stirring until a clear viscous swelling has formed.
II Dissolve components of phase B with slow stirring, pH 4 to 5.
III Add phase B to phase A and stir homogeneously.

EXAMPLE 7

Deodorant Emulsion

| A | Eumulgin B2 flakes | 1.0% |
|---|---|---|
|   | Ceteareth-20 | |
|   | Copolymer No. 35 | 1.0% |
|   | Cetiol 5 | 5.0% |
|   | Dioctylcyclohexane | |
|   | Cetiol OE | 5.0% |
|   | Dicaprylic ether | |
|   | Hydagen C.A.T. | 2.0% |
|   | Triethyl citrate | |
| B | Hydagen DCMF | 0.1% |
|   | Chitosan | |
|   | Glycolic acid | 0.04% |
|   | Distilled water | ad 100 |
|   | Preservative | 2.0% |

Preparation:
I Melt the components of phase A at 80° C. and homogenize.
II Dissolve components of phase B with stirring, and add slowly with stirring to A.
III Cool with stirring.
IV At 30° C. add preservative.

EXAMPLE 8

Crystal-clear Alcohol-free Gel

| A | DC 3225 C | 10.00% |
|---|---|---|
|   | Cyclomethicone/dimethicone copolyol | |
|   | DC 245 fluid | 3.40% |
|   | Cyclomethicone | |
|   | Polydimethylsiloxane | 3.9% |
|   | Dimethicone | |
|   | Copolymer No. 53 | 0.75% |
|   | Perfume 52847 | q.s |
| B | Rezal 36 G | 44.0% |
|   | Aluminum zirconium tetrachlorohydrex GLY | |
|   | Dipropylene glycol | 20% |
|   | Distilled water | ad 100 |

Preparation:
I Thoroughly mix components A and B separately.
II Add B to A.
III Homogenize.

EXAMPLE 9

O/W Antiperspirant Cream

| A | Copolymer No. 63 | 2.0% |
|---|---|---|
|   | Arlamol ISML | 2.0% |
|   | Isosorbide laurate | |
|   | Dow Corning 245 fluid | 2.0% |
|   | Cyclomethicone | |

-continued

| B | Distilled water | ad 100% |
| | Locron P (50%) | 40.0% |
| | Aluminum chlorohydrate | |
| | Preservative | q.s |
| | Perfume | q.s. |

Preparation:
I Mix the components of A.
II Add B to A with stirring.

What is claimed is:

1. A deodorant or antiperspirant which comprises at least one copolymer obtained by free-radical copolymerization of
   A) acryloyldimethyltaurine or acryloyldimethyltaurate or a mixture thereof,
   B) optionally, one or more further olefinically unsaturated, noncationic, comonomer which has at least one oxygen, nitrogen, sulfur or phosphorus atom and has a molecular weight of less than 500 g/mol,
   C) optionally, one or more olefinically unsaturated, cationic comonomer which has at least one oxygen, nitrogen, sulfur or phosphorus atom and possess a molecular weight of less than 500 g/mol,
   D) one or more silicon-containing component capable of free-radical polymerization and having a functionality of at least one, at least one silicon-containing component being a compound selected from the group consisting of

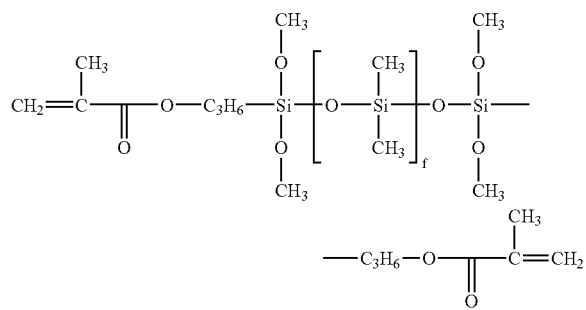

in which f=2 to 500,

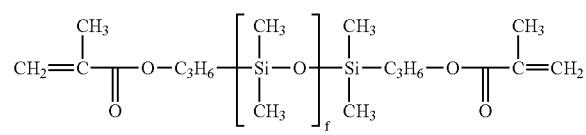

in which f=2 to 500,

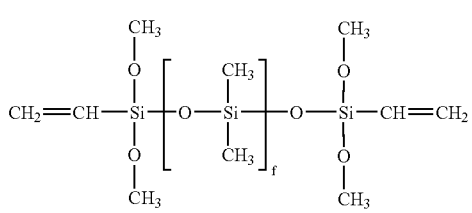

in which f=2–500, and mixtures thereof,

E) optionally, one or more fluorine-containing components capable of free-radical polymerization and having a functionality of at least one,
F) optionally, one or more olefinically mono- or polyunsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) fluorine-containing component E),
G) optionally the copolymerization taking place in the presence of at least one polymeric additive having number-average molecular weights of from 200 g/mol to $10^8$ g/mol, and at least one compound selected from the group consisting of glycerol, an active antimicrobial substance, an astringent, and mixtures thereof.

2. The deodorant or antiperspirant as claimed in claim 1, wherein the comonomer B) is selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate, styrene, acrylonitrile, vinyl chloride, vinylidene chloride, tetrafluoroethylene, vinylphosphonic acid or esters or salts thereof, vinylsulfonic acid or esters or salts thereof, allylphosphonic acid or esters or salts thereof, methallylsulfonic acid or esters or salts thereof, and mixtures thereof.

3. The deodorant or antiperspirant as claimed in claim 1, wherein the comonomer C) is selected from the group consisting of diallyldimethylammonium chloride (DADMAC), [2-methacryloyloxy)ethyl]trimethylammonium chloride (MAPTAC), [2-(acryloyloxy)ethyl)]trimethylammonium chloride, [2-methacryloyloxy)ethyl]trimethylammonium chloride, [2-(acryloyloxy)ethyl)]trimethylammonium chloride, N-methyl-2-vinylpyridinium chloride, N-methyl-4-vinylpyridinium chloride, dimethylaminoethyl methacrylate, dimethylaminopropylmethacrylamide, methacryloylethyl N-oxide, methacryloylethylbetaine, and mixtures thereof.

4. The deodorant or antiperspirant of claim 1, wherein the fluorine-containing component E) is a compound of formula (II)

where
R$^1$ represents a polymerizable function of a vinylically unsaturated compound; Y is a chemical bridge, and
r, s are stoichiometric coefficients which independently of one another are numbers between 0 and 200.

5. The deodorant or antiperspirant of claim 1, wherein the macromonomer F) is of formula (III)

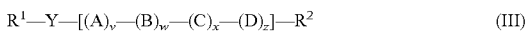

where R$^1$ represents a polymerizable function from a vinylically unsaturated compound;
Y is a bridging group;
A, B, C, and D independently of one another are discrete chemical repeating units;
v, w, x, and z independently of one another amount to from 0 to 500, the sum of v, w, x, and z being on average $\geq 1$; and $R^2$ is a linear or branched aliphatic, olefinic, cycloaliphatic, arylaliphatic or aromatic ($C_1$–$C_{50}$) hydrocarbon radical, OH, —$NH_2$ or —$N(CH_3)_2$ or is [—Y—$R^1$].

6. The deodorant or antiperspirant of claim 1, wherein the polymeric additive G) is selected from the group consisting of polyalkylene glycol, alkylpolyglycol, and mixtures thereof or a homopolymer or copolymer of a compound selected from the group consisting of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC), [2-(methacryloyloxy)ethyl]trimethylammonium chloride (MAPTAC); and mixtures thereof.

7. The deodorant or antiperspirant of claim 1, wherein the copolymerization takes place in the presence of at least one polymeric additive G).

8. The deodorant or antiperspirant of claim 1, wherein the copolymer is crosslinked.

9. The deodorant or antiperspirant of claim 1, wherein the copolymer is prepared by precipitation polymerization in tert-butanol.

10. The deodorant or antiperspirant of claim 1, wherein the copolymer is water-soluble or water-swellable.

11. The deodorant or antiperspirant of claim 1, which comprises, based on a finished composition, from 0.01 to 10% by weight of the copolymer.

12. The deodorant or antiperspirant of claim 1, which comprises from 0.01 to 89% by weight of water.

13. The deodorant or antiperspirant of claim 1, which comprises up to 10% by weight of glycerol.

14. The deodorant or antiperspirant of claim 1, which comprises an active antimicrobial substance.

15. The deodorant or antiperspirant of claim 1, which comprises astringent.

16. The deodorant or antiperspirant of claim 1, which is in the form selected from the group consisting of a lotion, cream, stick, multiphase stick, spray, roll-on preparation, and powder.

17. The deodorant or antiperspirant of claim 4 wherein $R^1$ is a radical selected from the group consisting of vinyl, allyl, methallyl, methylvinyl, acryloyl, crotonyl, senecionyl, itaconyl, maleyl, fumaryl, styryl, and mixtures thereof.

18. The deodorant or antiperspirant of claim 4, wherein the chemical bridge Y is selected from the group consisting of —O—, —C(O)—, —C(O)—O—, —S—, —O—$CH_2$—CH(O—)—$CH_2OH$, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$–$C_{50}$)alkyl-O—, —O-phenyl-O—, —O-benzyl-O—, —O—($CH_5$–$CH_8$)cycloalkyl-O—, —O—($C_1$–$C_{50}$)alkenyl-O—, —O—(CH($CH_3$)—$CH_2$—O)$_n$—, —O—($CH_2$—$CH_2$—O)$_n$—, —O—([CH—$CH_2$—O]$_n$—[$CH_2$—$CH_2$—O]$_m$)$_o$—, where n, m, and o independently of one another denote numbers from 0 to 200, and mixtures thereof.

19. The deodorant or antiperspirant of claim 5 wherein, $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

20. The deodorant or antiperspirant of claim 5, wherein the bridging group Y is selected from the group consisting of —O—, —S—, —C(O)—, —C(O)—O—, —O—$CH_2$—CH(O—)—$CH_2OH$, —O—$CH_2$—CH(OH)—$CH_2$O—, —O—$SO_2$—O—, —O—SO—O—, —PH—, —P($CH_3$)—, —$PO_3$—, —NH—, —N($CH_3$)—, and mixtures thereof.

21. The deodorant or antiperspirant of claim 5 wherein the discrete repeating units of A, B, C, and D are originating from a unit selected from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

22. The deodorant or antiperspirant of claim 5 wherein the discrete repeating units of A, B, C, and D are originating from a unit of ethylene oxide or propylene oxide.

23. The deodorant or antiperspirant of claim 5, wherein v, w, x, and z independently of one another amount to from 1 to 30.

24. A deodorant or antiperspirant which comprises at least one copolymer obtained by free-radical copolymerization of acryloyldimethyltaurine or acryloyldimethyltaurate or mixtures thereof and
   a) one or more silicon-containing component capable of free-radical polymerization and having a functionality of at least one, and selected from the group consisting of

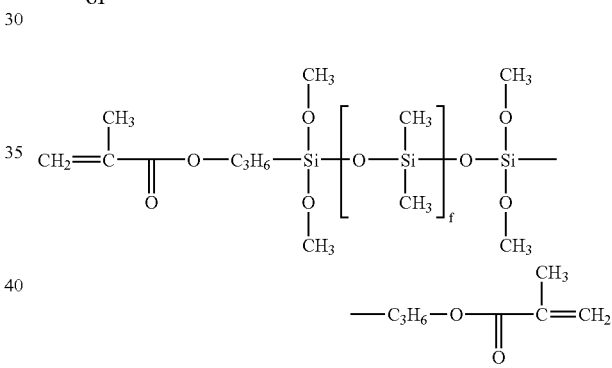

in which f=2 to 500,

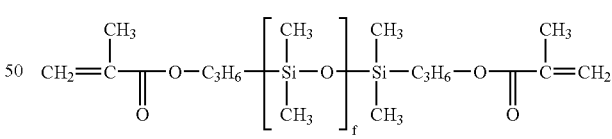

in which f=2 to 500,

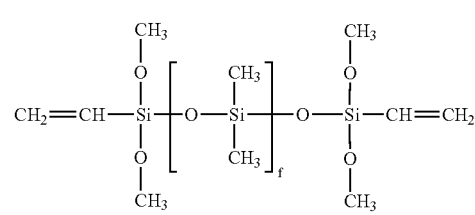

in which f=2–500, and mixtures thereof, with or in the presence of at least one component selected from the group consisting of:
b) one or more fluorine-containing component capable of free-radical polymerization and having a functionality of at least one,
c) one or more olefinically mono- or polyunsaturated, macromonomer each possessing at least one oxygen, nitrogen, sulfur or phosphorus atom and having a number-average molecular weight of greater than or equal to 200 g/mol, the macromonomer not being the silicon-containing component a) or the fluorine-containing component b), and
d) at least one polymeric additive having number-average molecular weights of from 200 g/mol to $10^9$ g/mol, and at least one compound selected from the group consisting of glycerol, an active antimicrobial substance, an astringent, and mixtures thereof.

25. The deodorant or antiperspirant of claim 24, wherein the copolymerization further comprises:
e) one or more further olefinically unsaturated, noncationic comonomer which has at least one oxygen, nitrogen, sulfur or phosphorus atom and has a molecular weight of less than 500 g/mol, or
f) one or more olefinically unsaturated, cationic comonomer which has at least one oxygen, nitrogen, sulfur or phosphorus atom and has a molecular weight of less than 500 g/mol.

26. The deodorant or antiperspirant of claim 24, wherein said macromonomer c) is crosslinking.

27. The deodorant or antiperspirant of claim 25, wherein said olefinically unsaturated, noncationic comonomer e) is crosslinking.

* * * * *